United States Patent
Damm et al.

(10) Patent No.: US 6,879,425 B2
(45) Date of Patent: Apr. 12, 2005

(54) DEVICE FOR DETERMINING AND/OR MONITORING THE DENSITY AND/OR THE LEVEL OF A FILLING MATERIAL IN A CONTAINER

(75) Inventors: Hartmut Damm, Schopfheim (DE); Joachim Neuhaus, Steinen (DE); Wolfgang Kämereit, Maulburg (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 0 days.

(21) Appl. No.: 10/362,523

(22) PCT Filed: Aug. 23, 2001

(86) PCT No.: PCT/EP01/09743

§ 371 (c)(1),
(2), (4) Date: Jul. 30, 2003

(87) PCT Pub. No.: WO02/18883

PCT Pub. Date: Mar. 7, 2002

(65) Prior Publication Data

US 2004/0025569 A1 Feb. 12, 2004

(30) Foreign Application Priority Data

Sep. 1, 2002 (DE) .......................................... 100 43 629

(51) Int. Cl.⁷ .......................... G02F 1/153; G01F 23/00; G01F 23/28; G01J 5/02
(52) U.S. Cl. ................ 359/272; 250/357.1; 250/339.12; 250/258; 250/395; 378/52; 378/54; 164/454
(58) Field of Search ........................ 359/272; 250/357.1, 250/252.1, 258, 339.12, 383; 378/52, 54; 164/454, 455; 340/635

(56) References Cited

U.S. PATENT DOCUMENTS

| | | | | |
|---|---|---|---|---|
| 3,100,841 A | * | 8/1963 | Reider ......................... 250/383 |
| 3,486,374 A | * | 12/1969 | Wright .......................... 378/54 |
| 3,594,575 A | | 7/1971 | Shoemaker ................... 378/52 |
| 4,369,368 A | * | 1/1983 | Bernard et al. ........... 250/357.1 |
| 4,591,719 A | | 5/1986 | Bonnemay ............... 250/357.1 |
| 5,218,202 A | * | 6/1993 | Evers ....................... 250/252.1 |
| 5,509,460 A | * | 4/1996 | Chun et al. ................. 164/454 |
| 5,646,409 A | * | 7/1997 | Leisinger et al. ........... 250/395 |
| 5,673,746 A | * | 10/1997 | Chun et al. ................. 164/454 |
| 5,859,590 A | * | 1/1999 | Otani ......................... 340/635 |
| 6,104,033 A | | 8/2000 | Graeme .................... 250/357.1 |
| 6,633,625 B1 | * | 10/2003 | Jackson et al. ............... 378/54 |

FOREIGN PATENT DOCUMENTS

| | | |
|---|---|---|
| DE | 1548959 | 12/1970 |
| DE | 2 008 411 | 9/1971 |
| DE | G8800444.9 | 3/1989 |
| DE | 3629965 | 12/1991 |
| DE | 19847555 | 4/2000 |
| DE | 19926388 | 12/2000 |

* cited by examiner

*Primary Examiner*—Loha Ben
(74) *Attorney, Agent, or Firm*—Bacon & Thomas

(57) ABSTRACT

The invention relates to a device for determining and/or monitoring the density and/or the level (L) of a filling material in a container. A transmitting unit which emits radioactive radiation and a receiving unit which is arranged in such a way that it receives the radioactive radiation or the secondary radiation that is produced by the interaction of the radioactive radiation with the filling material are provided. A regulating/evaluating unit which determines the density and/or the level of the filling material in the container using the measuring data that is supplied by the receiving unit is also provided. The aim of the invention is to provide a device which enables the level or the density of a filling material in a container to be measured reliably. To this end, the receiving unit consists of individual detector units. These detector units are positioned at different distances from the floor of the container, so that each detector unit directly or indirectly, essentially detects the proportion of radiation that passes.

18 Claims, 8 Drawing Sheets

µ = ln(S1/S2)

Figure 1:
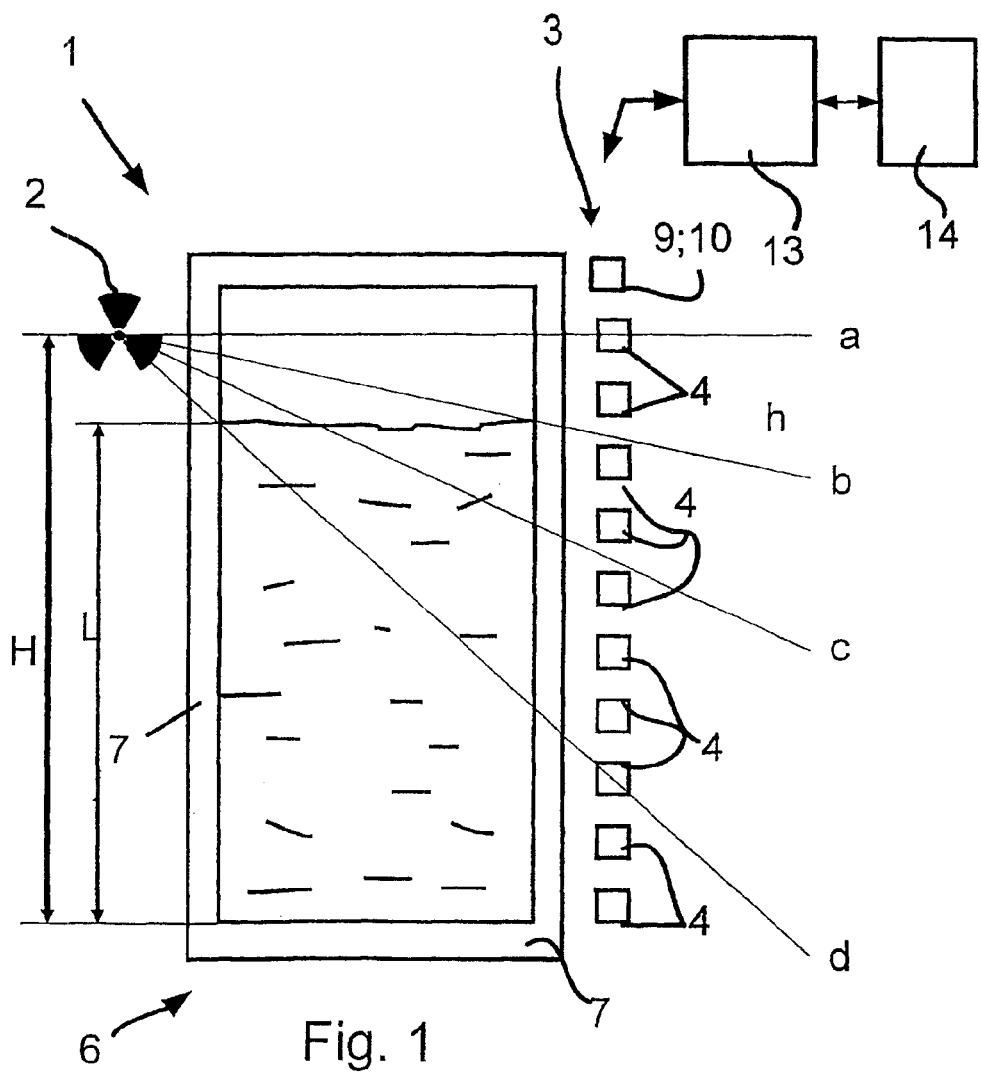

DEVICE FOR DETERMINING AND/OR MONITORING THE DENSITY AND/OR THE LEVEL OF A FILLING MATERIAL IN A CONTAINER

TECHNICAL FIELD

The invention relates to a device for determining and/or monitoring the density and/or the level of a filling material in a container.

The device has a transmitting unit that transmits radioactive radiation, and a receiving unit that is disposed such that it receives the radioactive radiation, or the secondary radiation generated by interaction of the radioactive radiation with the filling material, and a regulating/evaluating unit, which from the measurement data furnished by the receiving unit determines the density and/or the level of the filling material in the container.

The device of the invention further relates to a device in which the transmitting unit is unnecessary, since the filling material itself already transmits radioactive radiation that is subsequently detected by the receiving unit. This last feature of the invention can be employed for instance in measuring potassium concentration, in monitoring steel scrap for radioactive materials, and in monitoring packages and trucks for radioactive materials (for instance at boundaries between countries).

BACKGROUND

In radiometric level measurement or radiometric density measurement, ionizing radiation is passed through the container (tank or silo) in which the filling material is stored. In general there are two known kinds of built-on accessories: Either the radiation originates at a point-like transmitting unit at the upper edge of the container and is detected by a rod-shaped receiving unit (scintillator) which extends over the entire fill level on the opposite side of the container, or the transmitting unit is rod-shaped and the receiving unit is embodied as point-like. In the latter configuration, the receiving unit is preferably located in the upper region of the container.

The receiving unit is made of either plastic or a crystal. In either case, the gamma radiation arriving from the container or passing through the container is at least partly absorbed in the receiving unit. The absorbed radiation is partly output again in the form of UV light. Since in plastic the transmission of UV light is very slight, a wavelength shifter is typically incorporated into the plastic as well. This wavelength shifter converts the UV light into visible light (as a rule, blue or green light). The converted light can subsequently be converted into electrical signals, for instance by a photomultiplier. The electrical signals are then evaluated in an electronic circuit. For the sake of evaluation, in the normal situation, the normal of light pulses is counted. Another possible way of evaluation is to examine the amplitude spectrum, that is, the number of pulses, sorted by their amplitude. In both cases, it is always the entire radiation that has passed through the container and the filling material located in the container that is assessed. Depending on the level or density of the filling material, the proportion of the absorbed radiation is accordingly more or less high.

The known radiometric level measuring devices have the following disadvantages:

The outcome of measurement is affected by the temperature dependency and by the sensitivity of the detector.

If relatively long plastic rods are used as a receiving unit, then a large proportion of the light is absorbed; in that case, amplitude evaluation is of little use.

Extraneous sources that are not part of the measurement setup adulterate the outcome of measurement.

Different wall thicknesses of the container must be compensated for by complicated calculations.

Since the intensity of the radiation decreases with the square of the distance between the transmitting unit and the receiving unit, a linearization of the outcome of measurement must be performed.

Another disadvantage is that with increasing rod length, the angle of incidence of the radiation at the container wall becomes greater. This increases the travel length in the container wall and thus the absorption. Since the absorption function is exponential, this effect increases disproportionately greatly as the wall thickness increases.

Given the above relationships, the measurement accuracy of the system decreases with increasing distance from the transmitting unit, which means that the measurement accuracy is higher in the upper region of the container than in the lower region. The ratio of the fill level to the container diameter is limited to approximately 1/1. The consequence of this is that upon measurement over an extended range of levels, a plurality of transmitting units are needed. In approximate terms, it can be said that because of the absorption of the light in the plastic rod, the measurement range for a single detector unit is limited to approximately two meters.

SUMMARY OF THE INVENTION

The object of the invention is to provide a device which enables reliable measurement of the level or density of a filling material that is disposed in a container.

This object is attained in that the receiving unit comprises individual detector units, and the detector units are positioned at different distances from the floor of the container, so that each detector unit directly or indirectly detects essentially the proportion of radiation that passes through a defined partial area of the container or is generated in a defined partial area of the container. The primary advantage of the embodiment according to the invention is considered to be that it is now possible to arrive at an intensity profile over the entire fill level, or the fill level of interest, in the container.

In an advantageous refinement of the device of the invention, one detector unit is a solid detector and/or a liquid detector. In particular, it is possible to use a plastic scintillator or a crystal scintillator with a downstream photomultiplier or a downstream PIN diode as the detector unit. An ionization chamber can be used equally well as the detector unit. However, it is considered especially favorable if the detector unit is a semiconductor detector, such as a CdZnTe detector.

Semiconductor detectors are distinguished by a number of advantages, listed below:

No scintillation occurs; that is, there is no detour by way of light detection. Instead, the electrons released are evaluated directly in the semiconductor.

With a CdZnTe detector, energies up to 1.3 MeV (such as Co-60) can be measured.

Semiconductor detectors can be used up to a temperature of 70°.

No effects of aging are known so far, which means that semiconductor detectors are more stable than photomultipliers, for instance.

As bias voltages, values from 100 V to 300 V per millimeter of depth are needed. Voltage changes therefore affect the outcomes of measurement only slightly.

The bias voltage supply in semiconductor detectors, compared to photomultipliers, requires only very low power.

Semiconductor detectors are not hygroscopic and are chemically highly stable.

Semiconductor detectors have a linear temperature coefficient; temperature compensation is therefore easily possible electronically.

Semiconductor detectors are distinguished by high energy resolution and a compact structure.

Semiconductor detectors do not require a vacuum for operation; moreover, there is naturally also no risk of broken glass—which is a major problem with photomultipliers, for instance.

A disadvantage in certain uses of semiconductor detectors might be that because of the small structure—the typical crystal size is in the range of 15×15×3 mm—in contrast to an NaI crystal, for instance, they have relatively low sensitivity. However, this disadvantage can easily be overcome by providing that a detector unit is assembled from a plurality of individual detectors, and the individual detectors are disposed such that they form a detector array. For instance, four individual detectors are put together or interconnected to make a rectangular detector array. It is understood, however, that—depending on the application—it is also possible for the detector unit to comprise a single detector.

In an advantageous refinement of the device of the invention, at least a first additional detector unit is provided, which is disposed above a predetermined maximum level of the filling material in the container, and the first additional detector unit receives essentially only the radioactive radiation emitted by the transmitting unit that has not entered into interaction with the filling material. This additional detector unit can be used on the one hand to take the influence of the pressure prevailing in the part of the interior of the container that is free of filling material into account in measuring the level or density. Knowing the pressure is of major importance in the sense that the absorption of the radioactive radiation in gases is highly pressure-dependent. If the influence of pressure is known, the measurement data can be corrected accordingly. It is understood that instead of the first additional detector unit, a quite conventional pressure sensor can be used. Then care must merely be taken that the pressure sensor be located above the maximum level of the filling material in the container.

A preferred embodiment of the device of the invention provides a second additional detector unit, which is disposed such that it detects essentially only the radioactive background radiation in the immediate vicinity of the container. As a result, the influence of unwanted radioactive radiation sources can be detected, so that the level and density measurement data can be corrected accordingly.

As already noted above, one substantial advantage of the embodiment of the invention is that each individual detector unit receives only the radiation that is output in its direction. This makes it possible to set up an intensity profile over the entire level measurement range. Higher local resolution can furthermore be achieved by providing that between the measurement data furnished for instance by two detector units—the two detector units can for instance be next to one another—an interpolation is performed. Preferably, the distance between two successive detector units is designed variably, and the distance is adapted to whatever the desired local resolution is. It is understood that the distance between two successive detector units can also be kept constant over the entire level measurement range.

The embodiment of the device of the invention in which the detector units are disposed in a predetermined number on a retaining element has proved especially favorable. This facilitates mounting the receiving unit on the container wall or in the immediate vicinity of the container considerably. A preferred refinement of the device of the invention proposes that the retaining element is embodied flexibly. With a flexible embodiment, the receiving unit can be adapted without problems to any arbitrary shape of container.

Some detector units, such as photomultipliers, have a relatively strong temperature dependency. In this respect, it has proved highly advantageous if each detector unit is assigned a temperature sensor that determines the temperature of the measurement site. Because of the ascertained temperature measurement data, the regulating/evaluating unit can then take the temperature prevailing at the measurement site into account in evaluating the level or density measurement data. This option in turn leads to an improvement in measurement accuracy.

In a preferred refinement of the device of the invention, a bus line is provided, over which the detector units send their measurement data to the regulating/evaluating unit. In data transmission or data communication, it is understood that the known transmission standards can be used, such as Profibus PA, Fieldbus Foundation, etc.

An advantageous embodiment of the device of the invention proposes an input/output unit by way of which the operator can select an arbitrary detector unit to secure against overfilling; after that, via the input/output unit, the regulating/evaluating unit generates an appropriate report/warning as soon as the predetermined level is reached.

It has furthermore proved especially favorable if the regulating/evaluating unit determines the measurement data of the individual detector units with the container empty and sets up a corresponding empty profile; an analogous measurement profile is then obtained with the container filled. In a final step, the regulating/evaluating unit compares the measurement profile with the empty profile and can thus furnish information about the formation of foam above the filling material or the formation of scale on the container wall.

An advantageous refinement of the device of the invention furthermore proposes that the regulating/evaluating unit sets up a density profile of the filling material in the container and subsequently determines the level of filling material in the container, taking this density profile into account.

It is also provided that the regulating/evaluating unit sets up a density profile of the filling material disposed in the container, and that taking the density profile into account, the regulating/evaluating unit makes the density profile available to the operator for the sake of process analysis and/or for regulating purposes.

According to the invention, the object is also attained in that the receiving unit comprises two detector units, and the detector units are positioned in different positions along the container; that each detector unit directly or indirectly detects essentially the proportion of radiation that passes through a defined partial area of the container; and from the differing extinctions of the proportions of radiation that are detected in the two detector units, the regulating/evaluating unit determines the density of the medium in the container.

BRIEF DESCRIPTION OF THE INVENTION

The invention will be described in conjunction with the following drawings.

Figure 2:
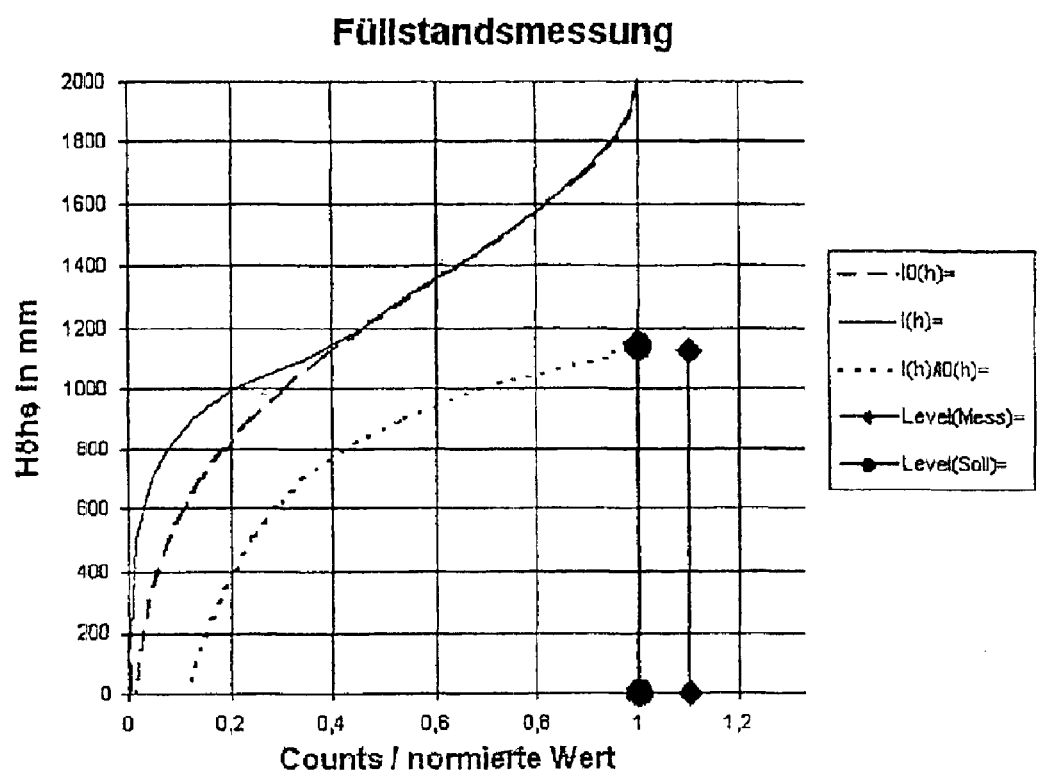
Figure 3:
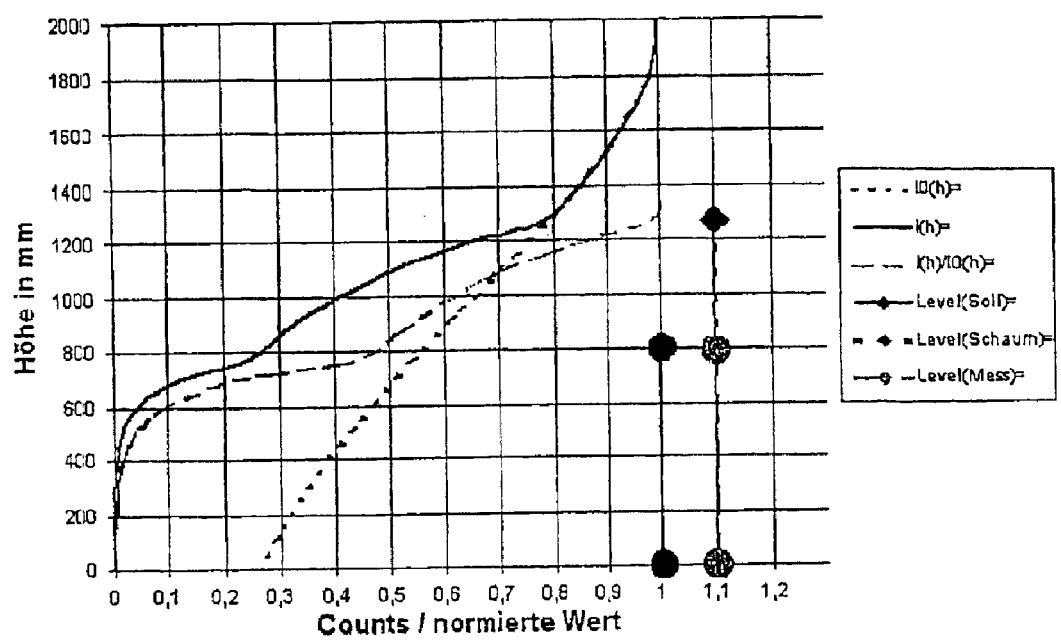
Figure 4:
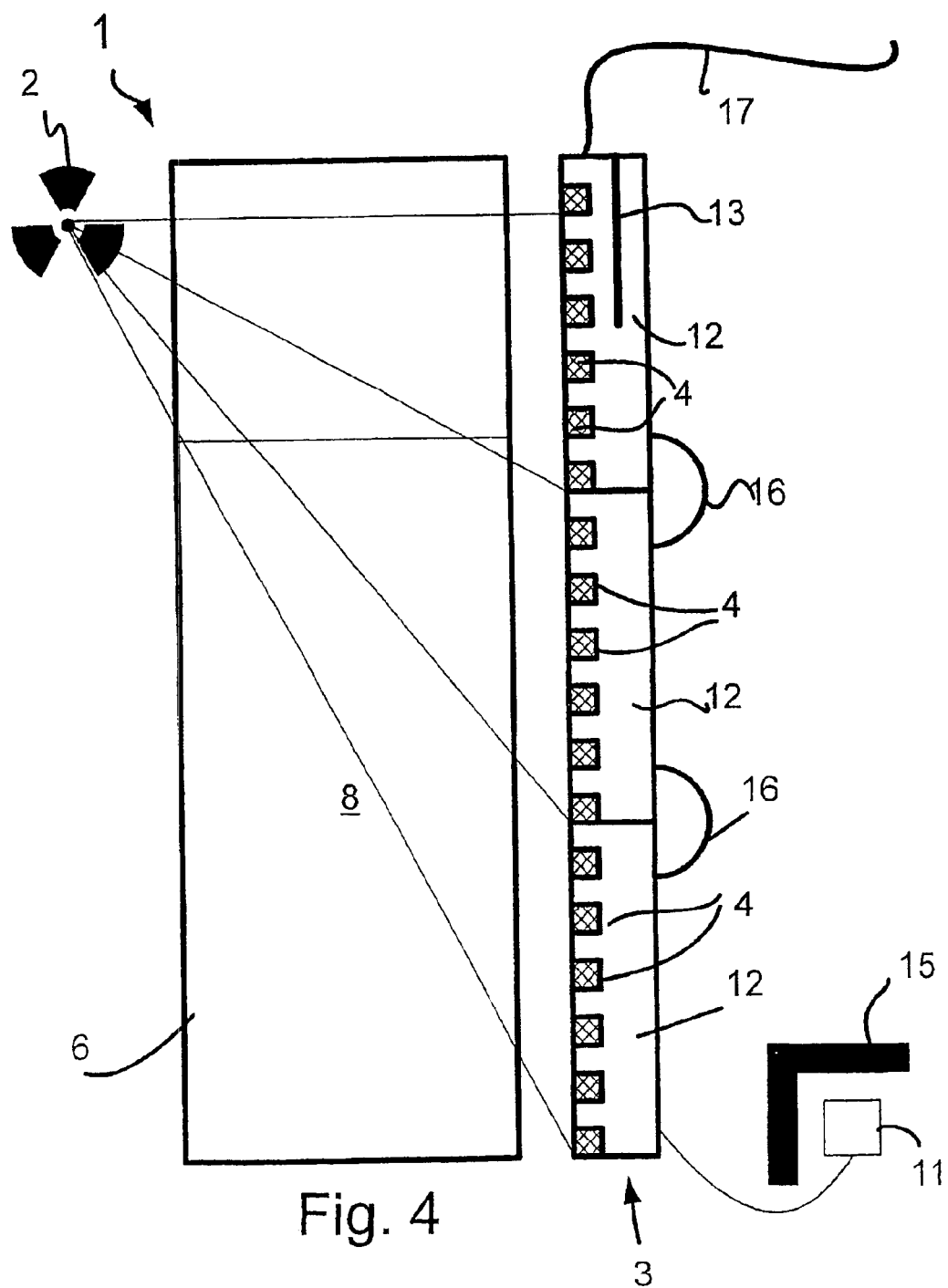
Figure 5:
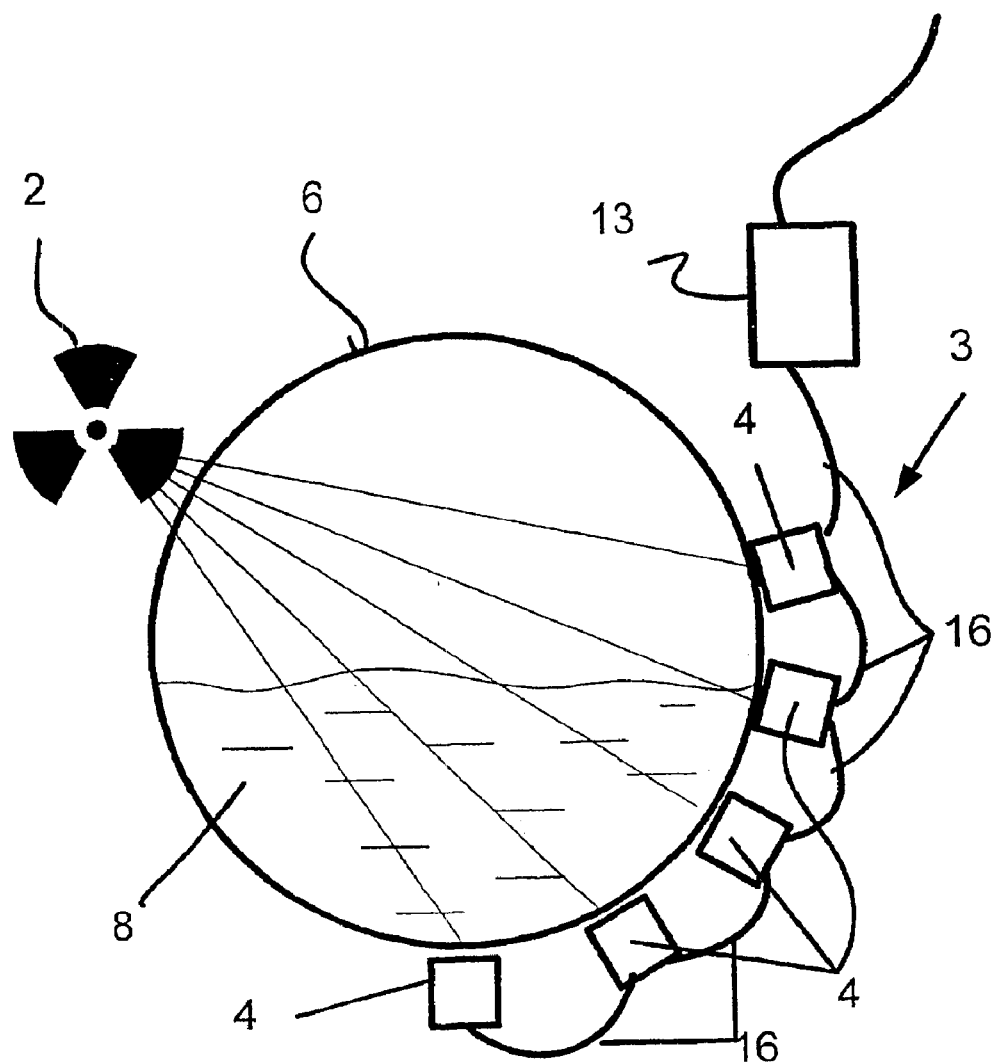
Figure 6:
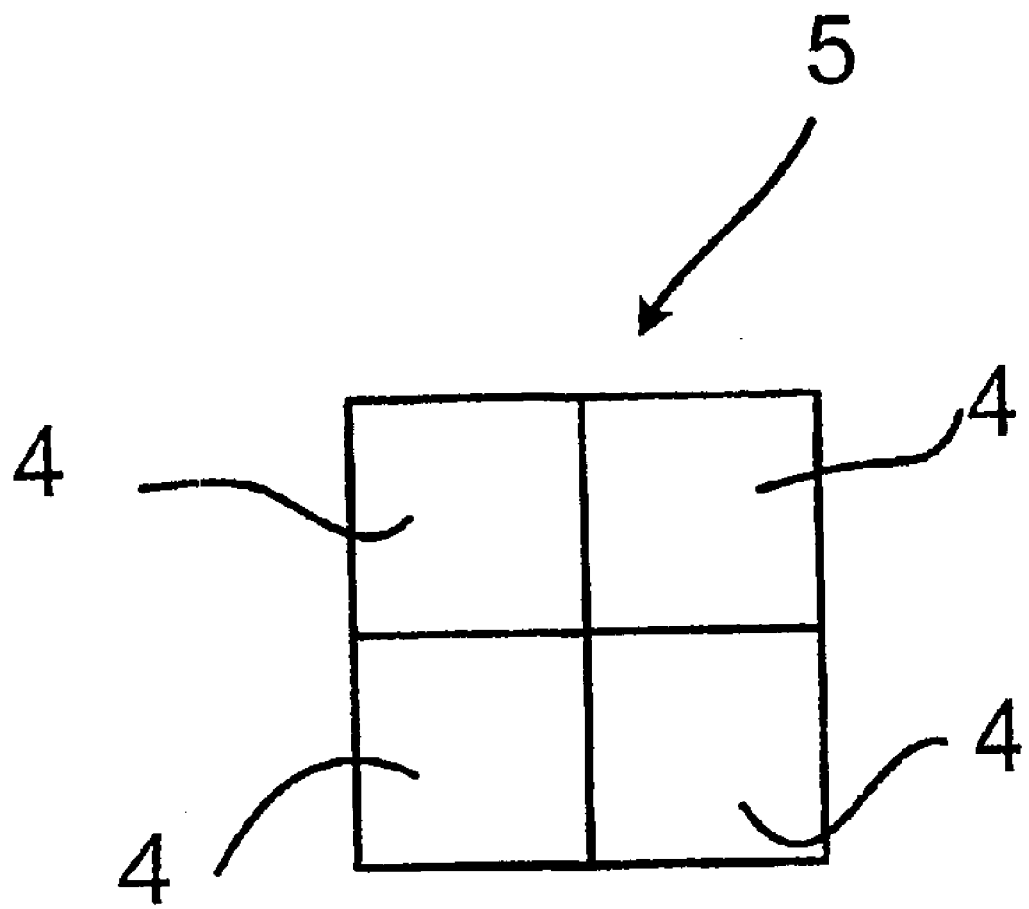
Figure 7:
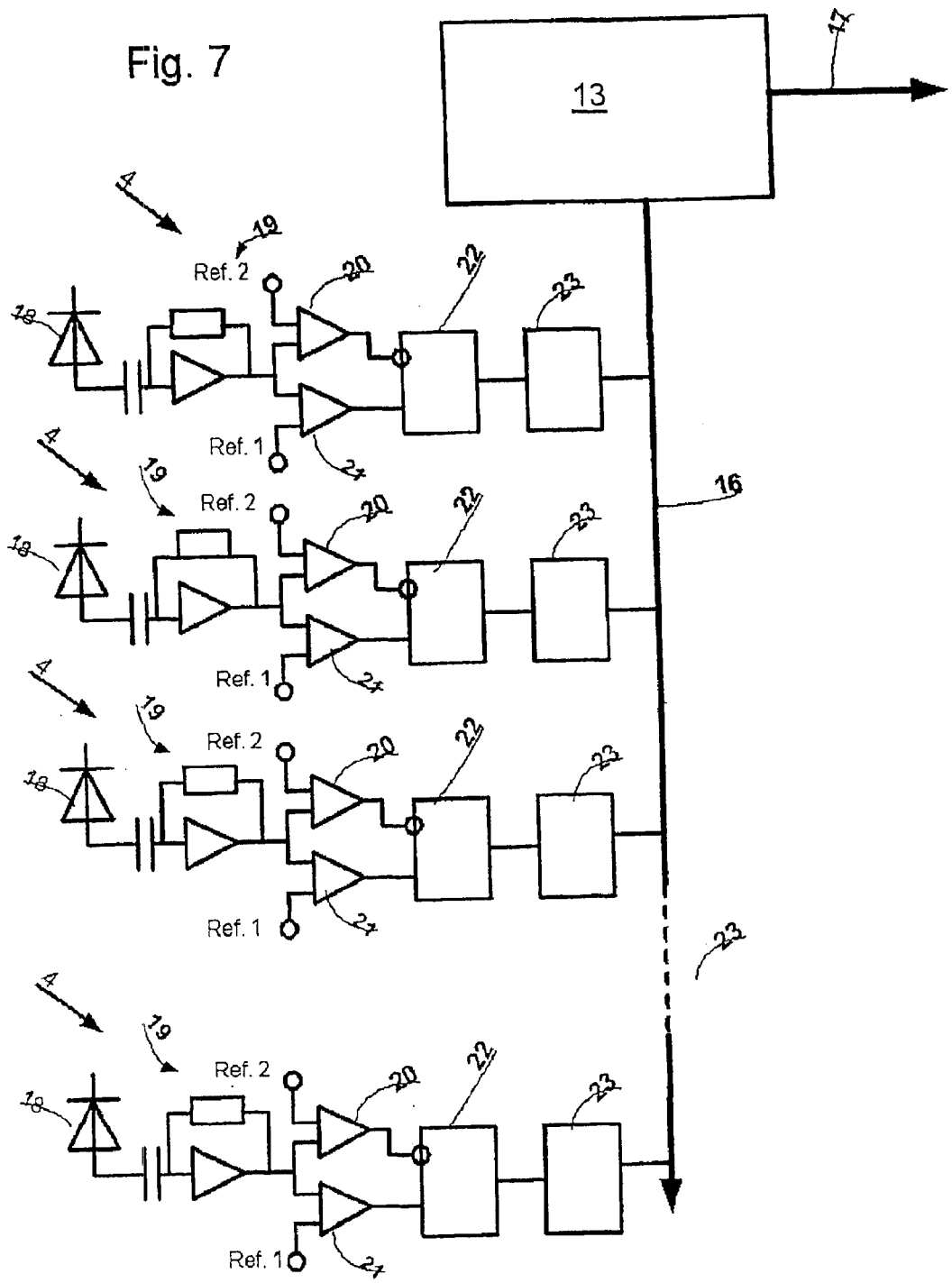
Figure 8:
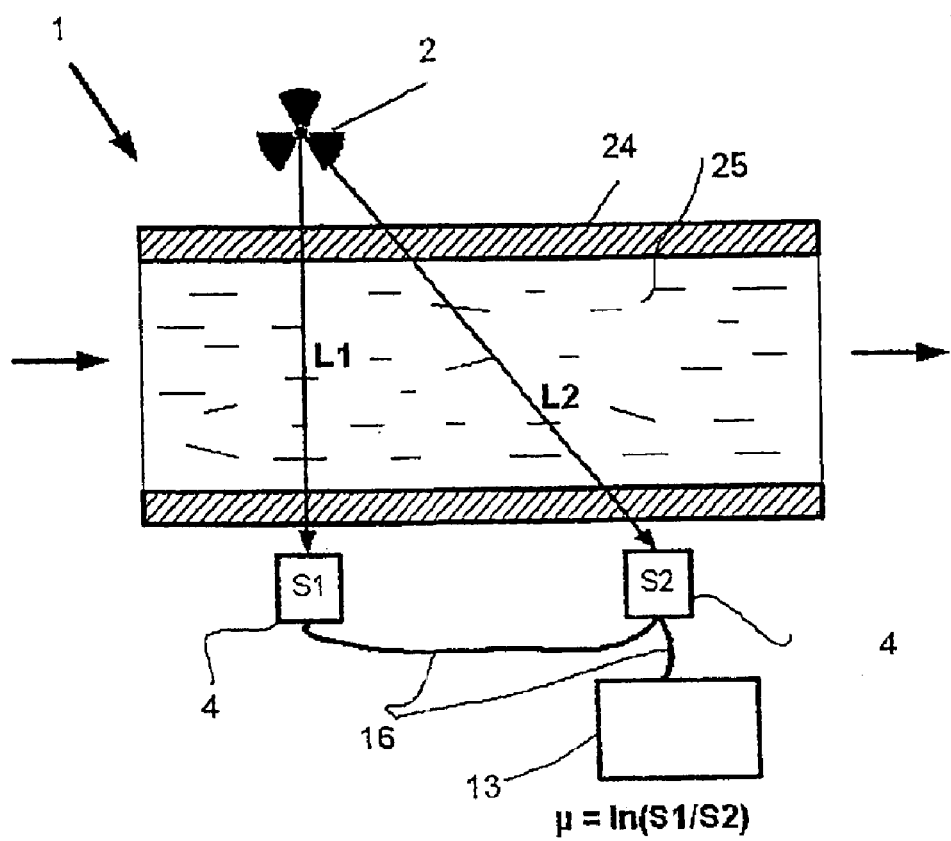

FIG. 1: is a schematic illustration of a first embodiment of the device of the invention;

FIG. 2: is a graph that shows the intensity profile with the container empty and the container filled;

FIG. 3: is a graph that shows the intensity profile with the container empty and the container filled in the case where foam develops on the filling material;

FIG. 4: is a schematic illustration of a second embodiment of the device of the invention;

FIG. 5: a schematic illustration of a third embodiment of the device of the invention;

FIG. 6: a plan view on a detector unit embodied as a detector array;

FIG. 7: is a block circuit diagram for one embodiment of the device of the invention; and FIG. 8: is an embodiment of the device of the invention for determining the density of a medium.

DESCRIPTION OF THE PREFERRED EMBODIMENTS

FIG. 1 shows a schematic illustration of a first embodiment of the device 1 of the invention. The filling material 8 is stored in the container 6. The fill level of the filling material 8 in the container 6 at the time is marked L.

A point-like transmitting unit 2 that transmits radioactive radiation is disposed in the upper region of the container 6. The radioactive radiation penetrates the container wall 7 and the interior of the container 6 and is received by the detector units 4 that are located on the opposite side of the container 6. The detector units 4 are either individual detectors or detector arrays 5, which are put together from a plurality of individual detectors. One possible embodiment of a detector array 5 is also shown in FIG. 6.

The lower-case letters a, b, c, d stand for instance for four different distances that the radiation travels through the container before it is received by the corresponding detector units 4. It is self-evident that the proportion of the radiation that reaches a detector unit 4 becomes less, the greater the distance that the radiation must travel through the filling material 8 and the container wall 7. In the case shown, this means concretely that the radiation marked a and b is received largely unattenuated, while the radiation that has taken the distances c and d has undergone more or less major absorption as a result of the interaction with the filling material 8.

Above the maximum possible level H, a first additional detector unit 9 is provided, which always receives radiation that has not entered into interaction with the filling material 8. This detector unit 9 serves to detect the proportion of radiation that is absorbed and that occurs as a result of pressure fluctuations in the part of the interior of the container 6 that is free of filling material.

FIG. 2 shows a graph which represents the intensity profile over the entire level H with an empty and a full container 6. As already noted above, by means of the device 1 of the invention, an intensity profile can be set up over the entire level or density measuring range, since every detector unit 4 receives only that radiation that is output in its direction by the transmitting unit 2. In FIG. 2, the following curves are also shown:

I(0): signal course with tank empty (zero curve)

I(h): signal course with partly filled tank (measurement curve)

I(h)/I0(h): division of the measurement curve by the zero curve

Level (desired): actual level L

Level (measured): level derived from the measurement curve

The procedure for how the actual level L is ascertained according to the invention is preferably as follows:

The first time the system is put into operation, a so-called zero calibration is performed. To that end, the zero curve is ascertained with the container 6 empty; the measurement data of the zero curve are stored in memory. Thus the zero curve reflects the course of intensity over the entire level measuring range with the container 6 empty. Next, with the container 6 filled, the actual level being marked L, the actual measurement curve is plotted. To determine the level, the measurement data for the actual measurement curve are divided by the corresponding measurement data for the zero curve. The result of the division, in the measuring range in which there is no filling material 8 present, is always equal to 1. In all measurement ranges in which there is filling material 8 present, the ascertained values are less than 1. The transition from 1 to values less than 1 thus corresponds to the actual level L in the container 6. The zero calibration moreover makes it possible to take the influence of the container geometry (for instance different wall thicknesses, flanges, or built-in fixtures in the container 6) into account automatically in determining the level or density.

To compensate for fluctuations in the radiation intensity of the transmitting unit or the influence of pressure fluctuations in the part of the interior of the container 6 that is free of filling material, the measured value of a first additional detector unit 9 is furthermore used for standardization. For the first additional detector unit 9 to furnish reliable measurement data, it must merely be assured that it be located above the maximum possible level H of the filling material 8 in the container 6.

FIG. 3 shows a graph representing the intensity profile with the container empty and the container full, in the case where foam forms on the filling material 8. Foam development occurs in many chemical processes and as a rule is unwanted, since it adulterates the measured level or density data. Moreover, with the radiometric measuring instruments known until now, foam detection was impossible. With the device of the invention, the foam can be detected from a second kink in the actual measurement curve. A corresponding signal can be sent to the operator via the regulating/evaluating unit 13 and the input/output unit 14.

Scale development on the container walls 7 can also be recognized from the fact that the typical course of the measurement curve changes.

In FIG. 4, a second embodiment of the device 1 of the invention is shown schematically. This embodiment differs from that shown in FIG. 1 in that a plurality of detector units 4 are each disposed on a respective retaining element 12, and the individual retaining elements 12 are positioned such that the detector units 4 can cover the entire measurement range. The cascading of the individual detectors is moreover done in the case illustrated via a bus line 16. The bus line 16 can connect both individually housed detector units 4 and multiple detector units 4 that form a detector array 5 or that are disposed on a retaining element 12 with one another. Because of this embodiment, for a fundamentally unlimited measurement range, only one regulating/evaluating unit 13 is required. The regulating/evaluating unit 13 interrogates the detector units 4 in succession and subsequently evaluates the measurement data forwarded.

Retroactive expansions of the measurement range can be done at any time without problems in this embodiment. The communication with a remote control point, not shown separately in FIG. 4, is effected via the bus line 17.

In FIG. 4, a second additional detector unit 11 can also be seen, which receives the background radiation in the immediate vicinity of the container 6. The measurement data furnished by the second additional detector unit 11 are likewise used for correction purposes.

FIG. 5 schematically shows a third embodiment of the device 1 of the invention. The difference from the embodiments shown in FIGS. 1 and 4 is primarily in the geometry of the container 6.

Besides measuring or monitoring the level of a filling material 8 in a container 6, the device of the invention is also—as already mentioned several times—excellently well suited to measuring or monitoring the density of a filling material 8. For the sake of clarity, the following example is referred to: In fluidized bed reactors, the density of the filling material 8, in the normal situation, is not constant above the level L. Because of the fluidization, gases or clouds of dust predominantly occur in the upper region of the container 6 or reactor, while in the lower region the filling material 8 is tightly packed. With conventional measuring instruments, this effect is taken only inadequately into account by assuming that the course of density corresponds with a predetermined characteristic linearization curve. The actual course of density over the level, however, is still ignored.

By means of the device of the invention, on the one hand the actual density course can be determined; on the other, however, it is also possible for the first time for the level to be determined exactly even when the density course is variable.

FIG. 7 shows a block circuit diagram of one embodiment of the device 1 of the invention. The proportion of radiation detected by a detector element 18—the detector element 18 is for instance a CdZnTe detector—is available in the form of a current measurement signal at the output of the detector element 18. The current measurement signal is amplified in the amplifier 19 (current to voltage converter). Next, the amplified measurement signal is supplied to the differentiator 20 and is supplied in parallel to the comparator 21. While the differentiator 20 removes the high-energy interference signals (such as cosmic radiation) from the measurement signal, the comparator 21 suppresses the low-energy noise components. The outputs of the differentiator 20 and comparator 21 are connected to the inputs of an AND gate 22. Consequently, at the output of the AND gate 22 there are only signals which are within an energy range defined by the symbols Ref. 1 and Ref. 2. The microprocessor 23 can for instance be a counter. The signals are carried to the regulating/evaluating unit 13 via a bus line 16.

In FIG. 8, one embodiment of the device 1 of the invention is shown for determining the density $\rho$ of a medium 25. In the case illustrated, the container 24 is a tube, through which a liquid medium 25, for instance, flows. The transmitting unit 2 is disposed on one side of the container 24. The transmitting unit 2 emits the radioactive radiation, which passes through the tube and the medium 25. Two detector units 4 are positioned on the opposite side of the container 24. The detector units 4 are disposed such that the radioactive radiation must travel different distances through the medium 25 before being detected by the two detector units 4. It is known that the intensity of radiation on passing through a medium 25 decreases exponentially. The extinction formula is $$I_{(d)} = I_0 \cdot e^{-\mu d}$$

in which I(d) is the measured intensity of the radiation once it has travelled the distance d through the medium 25 of density $\rho$, and $I_0$ is the output intensity of the transmitting unit 2, and $\mu$ describes the extinction factor.

Since the proportions of radiation have different intensities because of the different distances travelled through the medium 25, the extinction $\mu$ of the medium 25 can be determined by dividing the measured values of the two detector units 4. Since the extinction $\mu$ is a function of the density $\rho$ of the medium 25, the density $\rho$ of the medium 25 can consequently be ascertained.

What is claimed is:

1. A device for determining and/or monitoring the density and/or the level of a filling material in a container, the container defining a floor, comprising:
    a transmitting unit that transmits radioactive radiation;
    a receiving unit that is disposed such that it receives the radioactive radiation, or the secondary radiation generated by interaction of the radioactive radiation with the filling material; and
    a regulating/evaluating unit, which from the measurement data furnished by said receiving unit determines the density and/or the level of the filling material in the container, wherein:
    said receiving unit comprises individual detector units, said detector units are positioned at different distances from the floor of the container, so that each detector unit directly or indirectly detects essentially the proportion of radiation that passes through a defined partial area of the container or is generated in a defined partial area of the container.

2. The device of claim 1, wherein:
    one detector unit of said detector units is a solid detector and/or a liquid detector.

3. The device of claim 1, wherein:
    one detector unit of said detector units is one of: a plastic scintillator, a crystal scintillator with a downstream photomultiplier, and a downstream PIN diode.

4. The device of claim 1, wherein:
    one detector unit of said detector units is a semiconductor detector, including a CdZnTe detector.

5. The device of claim 1, wherein:
    said detector units comprise a single detector, and an assembly formed of a plurality of individual detectors that are disposed such that they form a detector array.

6. The device of claim 1, wherein:
    said receiving unit further comprises at least one first additional detector unit, which is disposed above a predetermined maximum level (H) of the filling material in the container, said first additional detector unit receives essentially only the radioactive radiation emitted by said transmitting unit that has not entered into interaction with the filling material.

7. The device of claim 6, further comprising:
    at least one second additional detector unit, which is disposed such that it detects essentially only the radioactive background radiation in the immediate vicinity of the container.

8. The device of claim 1, further comprising:
    a pressure sensor that is disposed above a maximum level (H) of the filling material in the container.

9. The device of claim 1, wherein:
    the distance between two successive detector units is designed variably, and the distance is adapted to whatever the desired local resolution is.

10. The device of claim 1, wherein:
    said receiving unit further comprises a retaining element, and wherein said detector units are disposed in a predetermined number on said retaining element, said retaining element is embodied flexibly.

11. The device of claim 1, wherein:

for the case where said detector units have a temperature dependency, each detector unit is assigned a temperature sensor, which determines the temperature at the measurement site; and wherein said regulating/evaluating unit takes the temperature prevailing at the measurement site into account in evaluating the measured level or density data.

12. The device of claim 1, further comprising:

a bus line by way of which said detector units and said regulating/evaluating unit communicate with a remote control point.

13. The device of claim 1, further comprising:

an input/output unit, by way of which the operator can select an arbitrary detector unit to secure against overfilling; and wherein said regulating/evaluating unit, via said input/output unit, outputs a report accordingly as soon as the predetermined level (L) is reached.

14. The device of claim 1, wherein:

said regulating/evaluating unit determines the measurement data of the individual detector units with the container empty and sets up a corresponding empty profile; said regulating/evaluating unit determines the measurement data of the individual detector units with the container full and sets up an actual measurement profile; and said regulating/evaluating unit, by comparison of the measurement profile with the empty profile, furnishes information about the formation of foam above the filling material or the formation of scale on the container wall.

15. The device of claim 1, said regulating/evaluating unit sets up a density profile of the filling material disposed in the container; and, taking the density profile into account, said regulating/evaluating unit determines the level (L) of the filling material in the container.

16. The device of claim 1, wherein: said regulating/evaluating unit sets up a density profile of the filling material disposed in the container; and, taking the density profile into account, said regulating/evaluating unit makes the density profile available to the operator for the sake of process analysis and/or for regulating purposes.

17. A device for determining and/or monitoring the density and/or the level of a radioactive filling material in a container, the container defining a floor, comprising:

a receiving unit which is disposed such that it receives the radiation of the radioactive filling material; and a regulating/evaluating unit, which from the measurement data furnished by said receiving unit determines the density and/or the level of the filling material in the container, wherein:

said receiving unit comprises individual detector units, said detector units being positioned at different distances from the floor of the container, so that each detector unit directly or indirectly detects essentially the proportion of radiation that passes through a defined partial area of the container or is generated in a defined partial area of the container.

18. A device for determining and/or monitoring the density of a medium in a container, comprising:

a transmitting unit that transmits radioactive radiation;

a receiving unit that is disposed such that it receives the radioactive radiation or the secondary radiation generated by interaction of the radioactive radiation with a filling material; and a regulating/evaluating unit being provided which from the measurement data furnished by said receiving unit determines the density of the medium in the container, wherein:

said receiving unit comprises two detector units, and said detector units are positioned in different positions along the container;

each detector unit directly or indirectly detects essentially the proportion of radiation that passes through a defined partial area of the container; and from the differing extinction of the proportions of radiation that are detected in said two detector units, said regulating/evaluating unit determines the density of the medium in the container.

* * * * *